(12) United States Patent
Steen

(10) Patent No.: US 8,980,541 B2
(45) Date of Patent: *Mar. 17, 2015

(54) EVALUATION AND PRESERVATION SOLUTION

(75) Inventor: Stig Steen, Lund (SE)

(73) Assignee: XVIVO Perfusion AB, Göteborg (SE)

( * ) Notice: Subject to any disclaimer, the term of this patent is extended or adjusted under 35 U.S.C. 154(b) by 921 days.

This patent is subject to a terminal disclaimer.

(21) Appl. No.: 13/178,655

(22) Filed: Jul. 8, 2011

(65) Prior Publication Data

US 2011/0269112 A1 Nov. 3, 2011

Related U.S. Application Data

(63) Continuation of application No. 11/889,460, filed on Aug. 13, 2007, now Pat. No. 8,012,677, which is a continuation of application No. 10/415,740, filed as application No. PCT/SE01/02419 on Nov. 5, 2001, now Pat. No. 7,255,983.

(60) Provisional application No. 60/279,725, filed on Mar. 30, 2001.

(30) Foreign Application Priority Data

Nov. 3, 2000 (SE) ...................................... 0004032

(51) Int. Cl.
*A01N 1/02* (2006.01)

(52) U.S. Cl.
CPC ................ *A01N 1/0226* (2013.01); *A01N 1/02* (2013.01); *Y10S 514/832* (2013.01)
USPC .......................... 435/1.2; 514/832; 435/284.1

(58) Field of Classification Search
CPC .................................................... A01N 1/0221
USPC ......................................................... 435/1.2
See application file for complete search history.

(56) References Cited

U.S. PATENT DOCUMENTS

| | | |
|---|---|---|
| 4,696,286 A | 9/1987 | Cochrum |
| 4,699,793 A | 10/1987 | Eguchi et al. |
| 4,798,824 A | 1/1989 | Belzer et al. |
| 4,920,044 A | 4/1990 | Bretan |
| 5,051,352 A | 9/1991 | Martindale et al. |
| 5,217,860 A | 6/1993 | Fahy et al. |
| 5,360,389 A | 11/1994 | Chenette |
| 5,571,801 A | 11/1996 | Segall et al. |
| 5,580,714 A | 12/1996 | Polovina |
| 5,643,712 A | 7/1997 | Brasile |
| 5,674,857 A | 10/1997 | Falk et al. |
| 5,699,793 A | 12/1997 | Brasile |
| 5,702,881 A | 12/1997 | Brasile |
| 5,759,764 A | 6/1998 | Polovina |
| 5,843,024 A | 12/1998 | Brasile |
| 5,948,609 A | 9/1999 | Carter et al. |
| 6,375,613 B1 | 4/2002 | Brasile |
| 7,255,983 B2 | 8/2007 | Steen |
| 2001/0009908 A1 | 7/2001 | Ponzin |

FOREIGN PATENT DOCUMENTS

| | | |
|---|---|---|
| DE | 940059 | 3/1956 |
| DE | 940059 C | 3/1956 |
| EP | 0556213 B1 | 8/1993 |
| WO | 9627287 A1 | 9/1996 |
| WO | 9827287 A1 | 9/1996 |
| WO | 9722244 A1 | 6/1997 |
| WO | 9737537 A1 | 10/1997 |
| WO | 9928348 A1 | 6/1999 |
| WO | 0046252 A1 | 8/2000 |
| WO | 0046253 A1 | 8/2000 |

OTHER PUBLICATIONS

STN International, File CAPLUS, CAPLUS Accession No. 1984:587541, document No. 101:187541, Karaeva, A.I., "Composition for preserving liver", SU, A1, 1109110, 19840823.
STN International, File CAPLUS, CAPLUS Accession No. 1992:79763, Document No. 116:79763, Adam, R. Astarcioglu et al.: "Ringer's lactate vs. serum albumin as a flush solution for UW preserved liver grafts: results of a prospective randomized study". Transplant. Proc. (1991), 23(5), 2374-5.
STN International, File CAPLUS, CAPLUS Accession No. 1992:79761, Document No. 116:79761, Schlumpf, hydroxyethylstarch, dextran, human albumin, and plasma proteins in a modified UW solution, Transplant. Proc (1991), 23(5), 2362-5.
WPI/Derwent's Abstract, Accession No. 1999-566277, week 9948, Abstract of JP 11246301 (Denki Kagaku Kogyo KK), Sep. 14, 1999.
Fiorante et al., "Low molecular weight dextran sulfate prevents complement activation and delays hyperacute rejection in pig-to-human xenotranplantation models", Xenotranplanation 8 (1): 24-35 (Feb. 2001).
Anaya-Prado et al., "The molecular events underlying ischemia/reperfusion injury", Transplantation Proceedings, 34 (7): 251802519 (2002) (abstract only).
Fuller et al., "Storage of cells and tissue at hypothermia for clinical use", Symposia of the Society for Experimental Biology, 41:341-61 (1987) (abstract only).
Meyer et al., "The therapeutic potential of nitric oxide in lung transplantation", Chest, 113 (5): 1360-1371 (1998), (abstract only).
Michel (1997) "Starling: the formulation of his hypothesis of microvascular fluid exchange and its significance after 100 years" Exp. Physiol. 82(1):1-30.
Steinbauer et al. (1997) "Effects of dextran on microvascular ischemia-reperfusion injury in striated muscle" Am. J. Physiol. 272:H1710-H1716.

(Continued)

*Primary Examiner* — Taeyoon Kim
*Assistant Examiner* — Tiffany Gough
(74) *Attorney, Agent, or Firm* — Pearne & Gordon LLP

(57) ABSTRACT

An evaluation and preservation solution for human and animal organs, tissues and parts thereof is described, wherein it comprises serum albumin at a concentration of 55-105 g/L, a scavenger and coating compound, preferably dextran compounds and derivatives thereof having essentially the same structure at a concentration of 1-55 g/L weight, and a physiological serum concentration of salts and nutrients in a physiologically acceptable medium.

24 Claims, 5 Drawing Sheets

(56) References Cited

OTHER PUBLICATIONS

Worning & Steven (1973) "Serum Protein concentration and oncotic pressure relationship in rat" Pflugers Arch. 340:77-80.

Garcia-Valdecasas 1998 "Liver conditioning after cardiac arrest: the use of normothermic reaction in an experimental animal model" Transpl Int 11:424-432.

Valero 2000 "Normothermic recirculation reduces primary graft dysfunction of kidneys obtained from non-heart-beating donors" Transpl. Int. 13:303-310.

Brasile 1999 "Ex vivo evaluation of organ function after cold ischemia" ASAIO J pp. 10-12.

Review of Medical Physiology, 18th Ed. 1997 Ganong ed., Appleton & Lange, excerpt providing table entitled "Ranges of Normal Values in Human Whole Blood (B), Plasma (P), or Serum (S)" (page number unknown), which is modified from Jordan et al., (1992) "Normal reference laboratory values" N. Engl J Med 327:718.

Nolte 1991 "Dextran and adenosine-coupled dextran reduce postishemic leukocyte adherence in postcapillary venules of the hamster" Capillary Functions and White Cell Interaction, Prog Appl. Microcirc 18:103-111.

Nolte 1992 "Reduction of postischemic leukocyte-endothelium interaction by dextran 70, but not hydroxyethylstarch 200/0.62" Int J Microcirc 11:210.

Ahlqvist 2004 "Equation for osmotic pressure of serum protein (fractions)" J Appl. Physiol 96:762-764.

Hoffman 1997 "Aktivierung neutrophiler granulozyten wahrend ishamie der lunge and reperfusion nach transplantation" Gefibchir, 11:108-114.

Menger 1995 "Microcirculatory disturbances secondary to ischemia-reperfusion" Transplant Proc. 27(5):2863-2865.

Murakami et al., "Inhaled Nitric Oxide and Pentoxifylline in Rat Lung Transplantation from Non-Heart-Beating Donors", J. Thorac. Cardiovasc. Surg. 113:821-829 (1997).

Hematological values in animals http://www.il-st-acad-sci.org/blood1.html (Mar. 2007).

"About dextran" http://www.dextra.net/dextran_physicalproperties.html (Mar. 2007).

Perfadex Vitrolife brochure (Apr. 2004).

Biancosino et al., "Acute toxicity of irinotecan in the ex-vivo isolated perfused human lung model high-dose therapy during isolated perfusion without acute toxic lung edema", Interact CardioVasc Thorac Surg, 2007; 6:583-587 (originally published online Jul. 4, 2007).

Inokawa et al., "Ex-vivo Perfusion and Ventilation of Rat Lungs From Non-Heart-Beating Donors Before Transplant", Ann Thorac Surg, Oct. 2006; 82:1219-1225.

STN International, File CAPLUS, CAPLUS Accession No. 1978:488033, document No. 89:88033, Jacobsen, I A.: "Continuous hypothermic perfusion of rabbit kidneys", Cryobiology (1978), 15(3), 290-301.

STN International, File CAPLUS, CAPLUS Accession No. 1973:476762, document No. 79:76762, Pegg, D.E. et al.: "Renal preservation by hypothermic perfusion. I. Importance of pressure control", Cryobiology (1973), 10(1), 56-66.

International Search Report issued in priority Application No. PCT/SE01/02419.

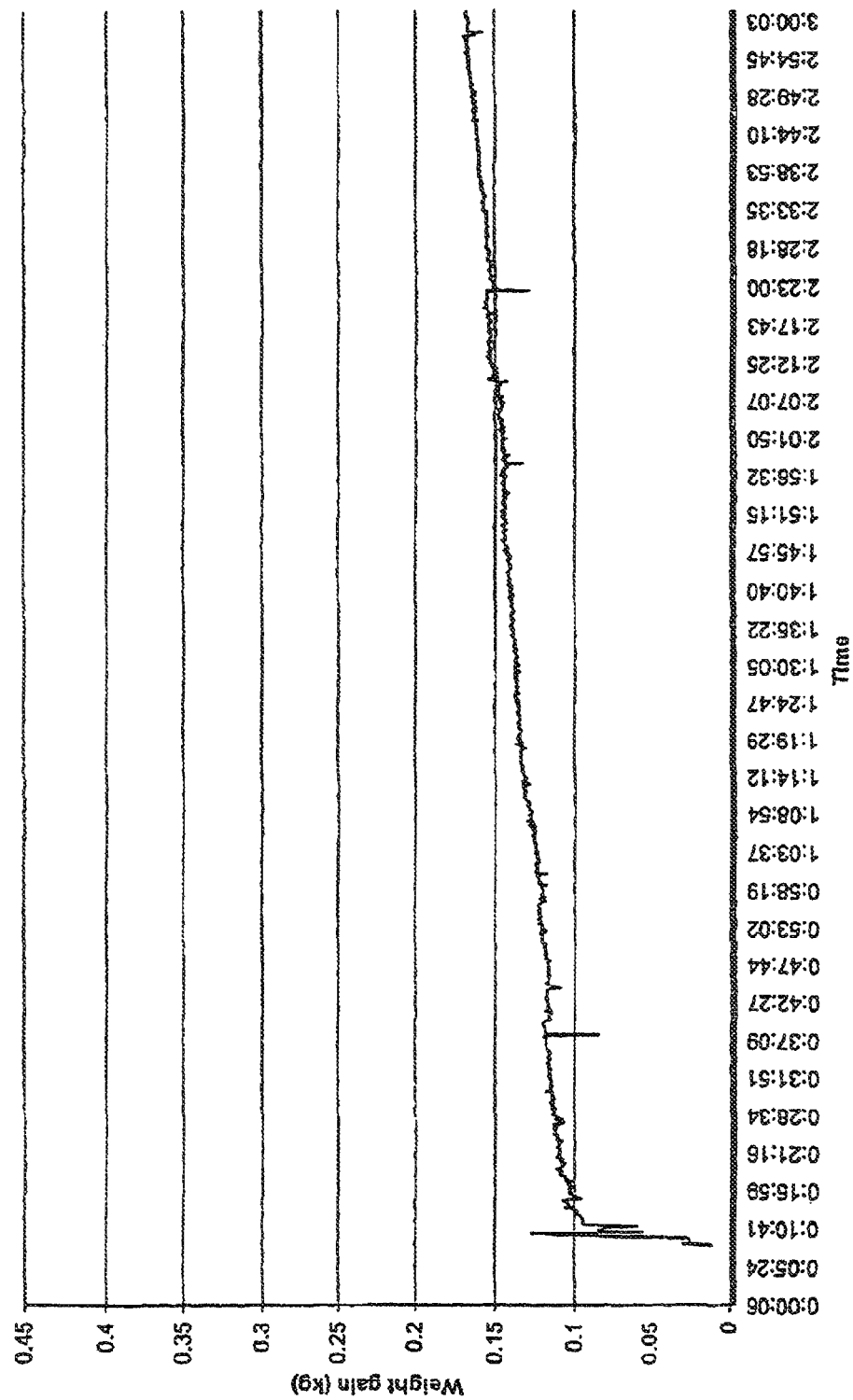

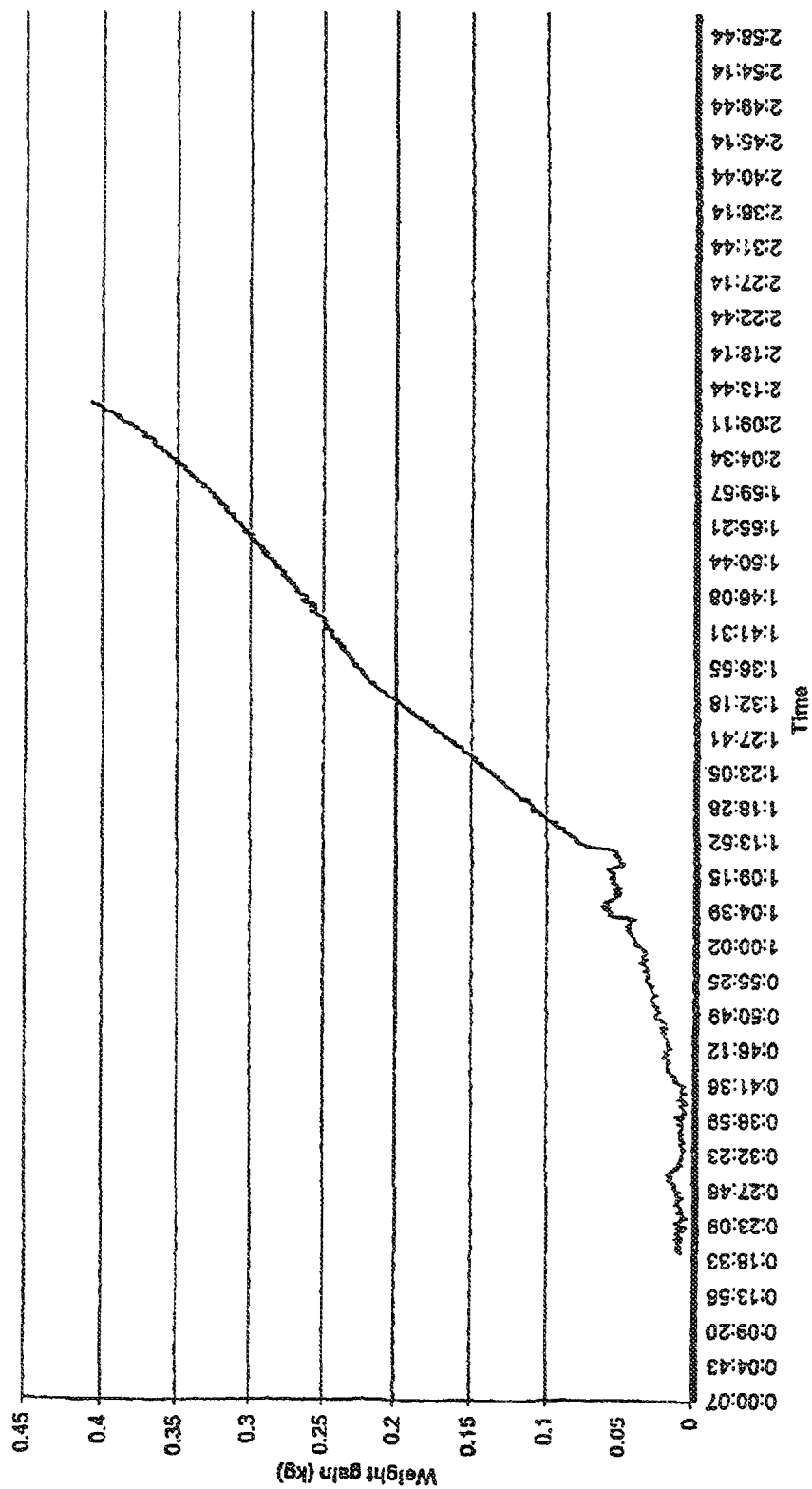

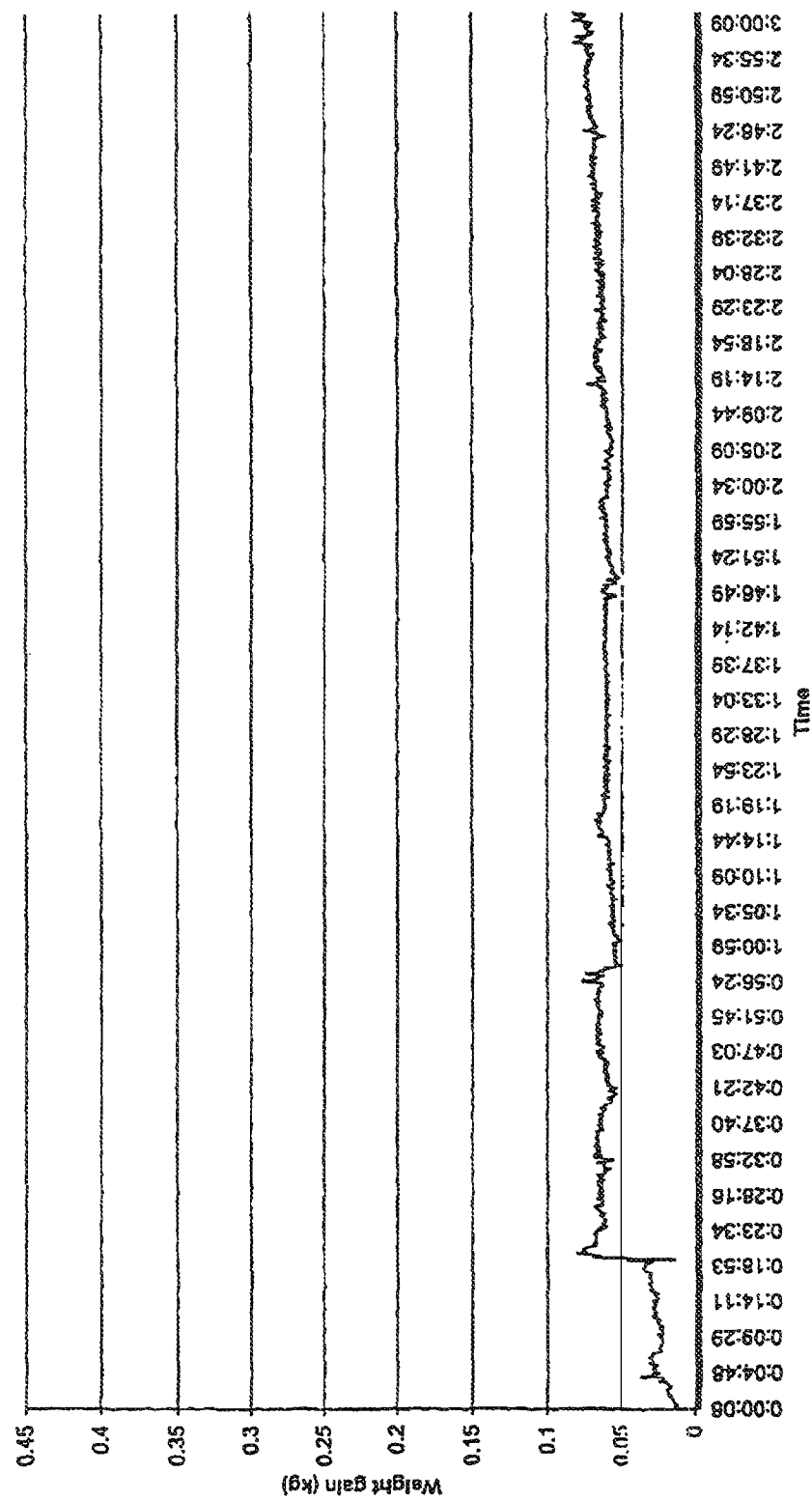

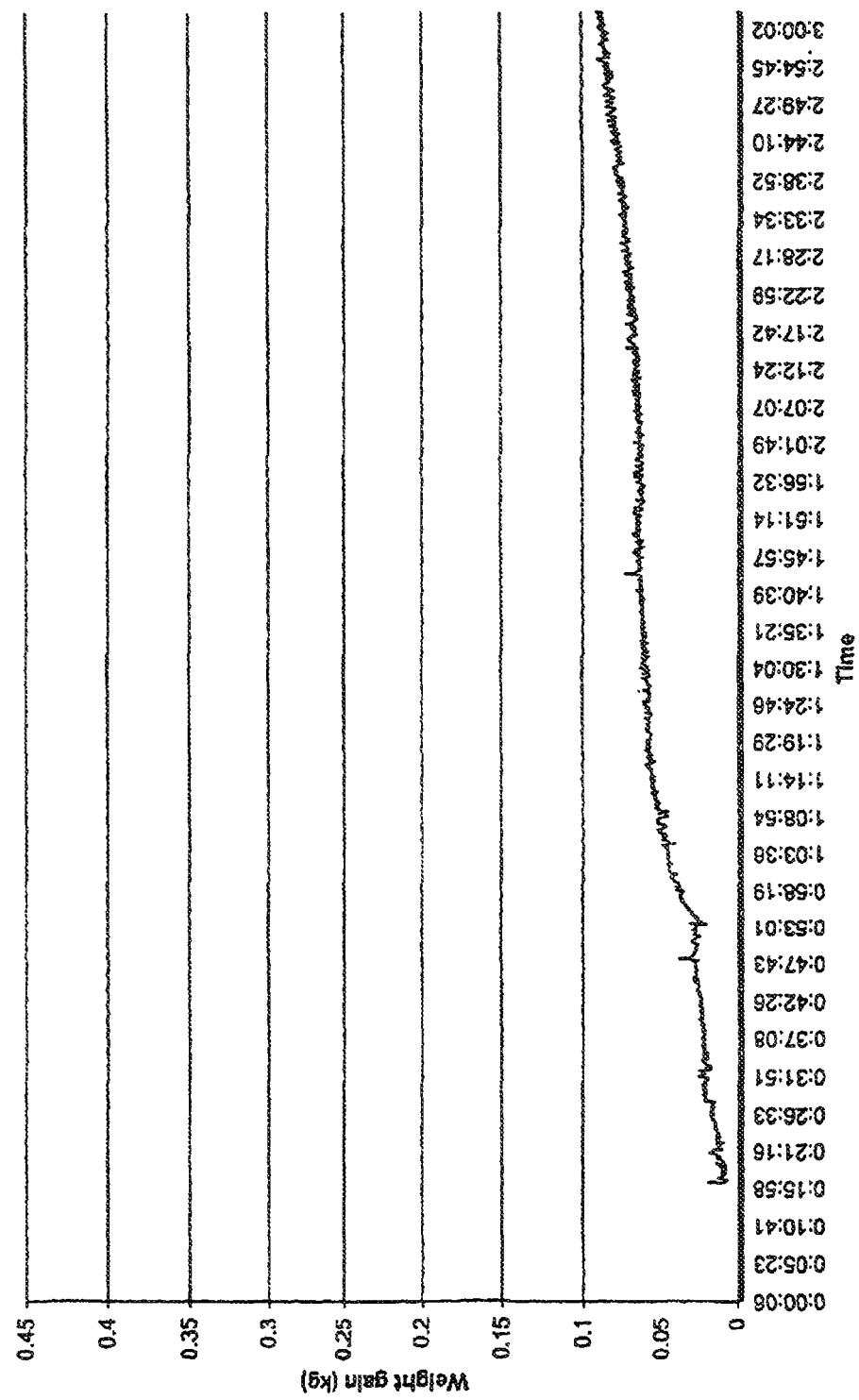

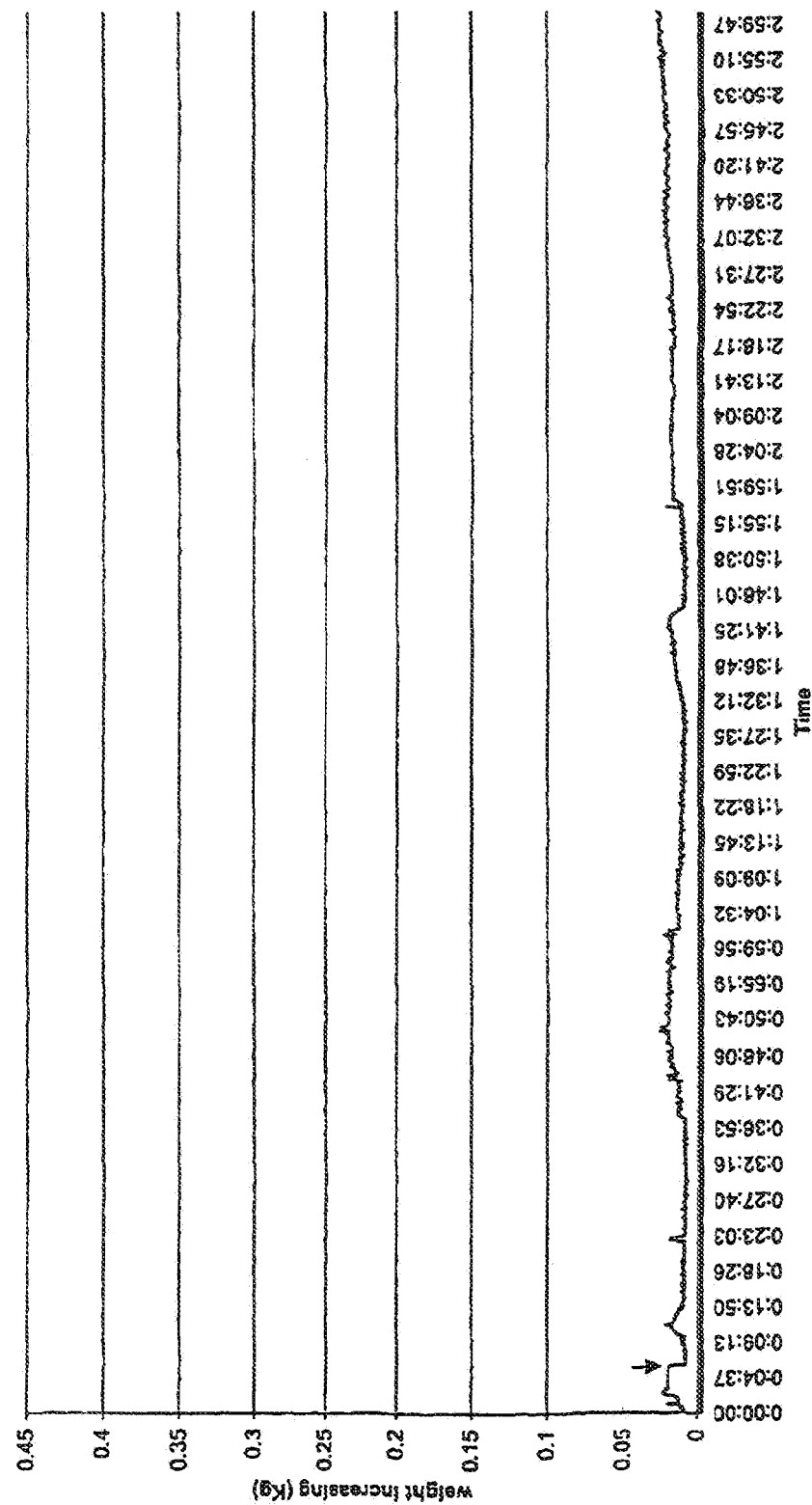

US 8,980,541 B2

EVALUATION AND PRESERVATION SOLUTION

CROSS-REFERENCE TO RELATED APPLICATIONS

This application is a continuation of U.S. application Ser. No. 11/889,460, filed Aug. 13, 2007, now U.S. Pat. No. 8,012,677, which is a continuation of U.S. application Ser. No. 10/415,740, filed Sep. 3, 2003, now U.S. Pat. No. 7,255,983, which was the National Stage of International Application No. PCT/SE2001/02419, filed Nov. 5, 2001, which claims the benefit of U.S. Provisional Application No. 60/279,725, filed Mar. 30, 2001. This application also claims foreign priority from Swedish Application No. 0004032-9, filed Nov. 3, 2000. Each of the above-listed applications is incorporated herein by reference.

FIELD OF INVENTION

The present invention relates to an evaluation and preservation solution for human and animal organs and tissues and parts thereof for transplantation, to a method for evaluation of such organs and tissues and parts thereof before transplantation, and to a method for transplantation from a non-heart-beating donor.

BACKGROUND ART

In clinical organ transplantation today kidneys, livers, hearts and lungs are the common transplanted organs. Pancreas is still not very often transplanted, and transplantation of small bowels and other organs are at the experimental stage. Regarding the preservation of kidneys, livers, hearts and lungs, the golden standard is cold ischemic preservation. This means that the organ which is to be preserved is flushed with a cold preservation solution and after that the organ is immersed in the same cold solution until it can be transplanted. The most common organ preservation solution used today is the University of Wisconsin solution (UW). For the preservation of kidneys and livers UW is the most frequently used preservation solution. Even for hearts it is used more and more, but for hearts St Thomas solution in different modifications is still the most common solution. A new solution used in heart preservation in the last few years is Celsior, which is a solution very similar to UW, except that the potassium concentration is much lower. For lungs Euro-Collins solution is still the most frequently used solution, but Perfadex is used increasingly. What all these solutions have in common is that initially stated, i.e. that the organs are flushed with a cold solution and after that immersed in the same cold solution. For kidneys and livers good preservation for up to 24 hours is obtained clinically, for lungs most trans-plant surgeons accept 6 hours and for hearts 4 hours of cold ischemic time. The organs to be transplanted have hitherto been obtained from so called brain-dead but heart-beating donors or from non-heart-beating persons within minutes after death, where the possibilities for acute harvesting and permission from next of kin to do it happened to be present; such cases are rare, and will not solve the donor organ shortage. This is also accepted for livers and kidneys. However, if organ donation from non-heart-beating donors will be a controlled clinical procedure, there is a need for an evaluation/preservation solution for organs from non-heart-beating donors, but so far no satisfactory solutions for this purpose have been produced. If this problem of lack of a convenient solution of this type could be solved, a larger number of organs would be available for transplantation, and the problem of lacking organs could be substantially eliminated. At the moment, thousands of people world-wide are dying or suffering while waiting for organs for transplantation. None of the solutions in use at present for cold ischemic preservation could be used as evaluation solutions for organs from a non-heart-beating donor. University of Wisconsin solution and Euro-Collins solution have an intracellular potassium content, which gives vascular spasm at normothermia, and the same will St Thomas and Celsior do, although not to the same degree. Perfadex, which is a low potassium-dextran solution and could be used if mixed with erythrocytes, has not the oncotic pressure necessary for perfusing, e.g. lungs without oedema development.

OBJECT OF THE INVENTION

The object of the present invention is to solve the above-mentioned problem of lack of a solution which makes evaluation and preservation of human and animal organs, tissues and parts thereof for transplantation, particularly from non-heart-beating donors, possible.

This object is achieved by a combined evaluation and preservation solution which is of the type mentioned by way of introduction and which is defined in the characterising part of the independent claim. Preferred embodiments of the present invention are defined in the dependent claims.

The present invention also relates to a mixed solution ready for use comprising the evaluation and preservation solution and red blood cells.

The present invention also relates to a method for the evaluation of human and animal organs, tissues and parts thereof before transplantation and to a method for transplantation from a non-heart-beating donor.

The present invention also relates to use of the above-mentioned evaluation and preservation solution for the evaluation and preservation of organs, tissues and parts thereof before transplantation.

DESCRIPTION OF THE DRAWINGS

FIG. 1 shows schematically a lung perfusion test with an evaluation and preservation solution, which in connection with the test and drawings is called evaluation solution for short, lacking both Dextran 40 and serum albumin, as a function of the weight gain (expressed in kg) of the lung and time.

FIG. 2 shows schematically a lung perfusion test with an evaluation solution with 50 g/L Dextran 40, but without human serum albumin, as a function of the weight gain (expressed in kg) of the lung and time.

FIG. 3 shows schematically a lung perfusion test with an evaluation solution with 70 g/L of human serum albumin but without Dextran 40 as a function of the weight gain (expressed in kg) of the lung and time.

FIG. 4 shows schematically a lung perfusion test with an evaluation solution containing 35 g/L of human serum albumin and 25 g/L of Dextran 40 as a function of the weight gain (expressed in kg) of the lung and time.

FIG. 5 shows schematically a lung perfusion test with an evaluation solution containing 70 g/L of human serum albumin and 5 g/L of Dextran 40 as a function of the weight gain (expressed in kg) of the lung and time.

SUMMARY OF THE INVENTION

After extensive studies and experiments, the inventor has concluded that to be able to perfuse organs from a non-heart-beating donor and evaluate them at normothermia, the solution used must have a physiological oncotic pressure. Otherwise oedema will develop. The buffers and electrolyte concentration in such a solution has to be similar to those in plasma and be compatible with red blood cells. (Perfusion at 37° C. without oxygenated red blood cells would destroy the organ due to warm ischemia). Further, the solution should also contain compounds opening up the capillary microcirculation. Further, the inventor has realised that the presence of a compound coating the endothelium, scavenging undesired substances and having detoxifying activity is required. Another requirement is that the solution after the organ or tissue perfusion/evaluation step is able to act as a satisfactory preservation solution, so that it can be used for cold ischemic storage after the evaluation, if that would be the most practical way to transport the organ to the receiver.

The evaluation and preservation solution for human and animal organs, tissues and parts thereof comprises serum albumin at a concentration of 55-105 g/L, a scavenger and coating compound, preferably dextran molecules and derivatives thereof at a concentration of about 1-55 g/L, together with physiological serum concentrations of salts and nutrients in a physiologically acceptable medium. Preferably, the evaluation and preservation solution according to the present invention comprises 65-85 g/L, most preferably about 75 g/L, of human serum albumin.

Preferably, the evaluation and preservation solution according to the present invention comprises a dextran compound in a concentration of 2-20 g/L, most preferably 5 g/L, and Dextran 40 is most preferred. Other examples of commercially available useful dextran molecules are Dextran 60 and Dextran 70.

The salts contained in the solution according to the present, invention comprise sodium, potassium, calcium, magnesium, phosphate, hydrogen carbonate, and chloride ions, and the nutrients comprise physiologically acceptable carbohydrates, preferably glucose; fatty acids, e.g. essential fatty acids, and amino acids, e.g. essential amino acids. The solution according to the present invention may also contain a vasodilator, preferably papaverin; antibiotics; fibrinolytic components, such as Actilyse, also called "altepas" (human tissue plasminogen activator), and thrombocyte receptor blockers, such as Reopro, also called "abciximab". For long-term perfusion the solution according to the present invention may contain hormones, e.g. tyroxin/triiodotyronin, insulin, cortison, growth hormone, and anabolic steroids, in physiological concentrations.

Red blood cells in a serum solution are added separately to and mixed with the above described solution according to the present invention just before the perfusion step. This mixed solution, also referred to as "artificial serum solution", based on the evaluation and preservation solution according to the present invention and the red blood cell containing solution is to be perfused into the organ, tissue or part thereof to be evaluated and represents one embodiment of the present invention, in the following referred to as "mixed solution ready for use according to the present invention" or, shortly, "solution ready for use".

The concentration of the ingredients present in the evaluation and preservation solution according to the present invention is expressed in g/L of the solution to be mixed with the serum solution containing red blood cells. The concentration of the ingredients present in the mixed solution ready for use according to the present invention, i.e. the solution to be directly applied to or to perfuse the organ, tissue or part thereof to be evaluated and optionally preserved before transplantation, is expressed in g/L of the "artificial serum solution". When mixing the evaluation and preservation solution according to the present invention with the serum solution containing red blood cells, the concentration of the ingredients of the original evaluation and preservation solution is slightly reduced due to a small dilution effect, as appears from the concentration data presented in the following. This dilution effect is generally about 8% and affects in principle only the higher values in the concentration intervals presented.

The expression "organs, tissues and parts thereof" used throughout the application text means all parts of the body which can be transplanted at present and in the future.

The expression "non-heart-beating donor" used throughout the application text means a patient for which the heart has been irreversibly arrested and brain death has been assumed, i.e. a hands off period of minimum 1.0 minutes at normothermia after the diagnosis of irreversible heart arrest.

The expression "serum albumin" used throughout the application text means albumin derived or purified from a human or animal serum source or recombinant serum albumin produced by genetic engineering. Any derivatives and analogues thereof having essentially the same physical action in the present invention are also contemplated to be included in this expression.

The expression "physiological serum concentration" used throughout the present application text means serum concentrations of the substances in question which exactly or essentially correspond to the normal serum concentration in human and animal blood.

The term "lung(s)" used throughout the application text includes the whole lung(s) including bronchi and also lobes and segments thereof.

Serum albumin is a water-soluble plasma protein. It is produced in the liver and is important for the oncotic pressure, also called the colloidosmotic pressure, of the blood, i.e. it has the capability of maintaining the plasma of the blood within the vessels. It also act as a transport protein for many substances, e.g. fatty acids. The serum albumin is negatively charged and is surrounded with sodium ions. Therefore, it is very difficult for the serum albumin to pass through the capillary wall. The oncotic pressure in the blood is normally maintained at a level of 25 mm Hg. E.g. human serum albumin, having a molecular weight (Mw) of 69,000, is too large to pass out through the semi-permeable capillary walls, and the concentration thereof is normally about 45 g/L blood. As it is negatively charged, serum albumin attracts sodium ions, and this add about 7 mm Hg to the oncotic pressure (the so-called Donnan effect). The hydrostatic pressure in the arterial end of the capillaries is normally about 30 mm Hg, and the hydrostatic pressure in the venous end of the capillaries is normally about 10-15 mm Hg. As stated above, an intermediate oncotic pressure of about 25 mm Hg exists in the capillaries, making water to leave in the arterial end and return in the venous end.

As the serum albumin is responsible for the maintenance of the correct oncotic pressure, it has an important function as a colloidosmotically active substance, providing about 70% of the oncotic pressure. If a solution containing a satisfactory electrolyte composition mimicing that in normal plasma, but without colloidosmotically active substances, it would immediately create a weight gain due to oedema formation in the organ to be transplanted. As normal human plasma also contains gamma globulins and other protein molecules, providing about 30% of the oncotic pressure, the present inventor found that the solution according to the present invention should not only contain serum albumin, but also in an increased amount with a view to compensating for the oncotic pressure normally induced by the gamma globulins and other protein molecules, which are absent in the solution according to the present invention. In an aqueous test solution containing normal extra-cellular concentrations of sodium, potassium, calcium, magnesium, chlorine, hydrogen carbonate, phosphate and glucose and having a normal osmolarity of about 290, different concentrations of human serum albumin have been tested on lungs. At a concentration of about 70 g/L in the solution ready for use, the best results were obtained, i.e. the lungs were perfused without oedema formation. The oncotic pressure in this test solution was about 25 mm Hg, i.e. corresponding to the oncotic pressure in normal lung capillaries. Satisfactory results can be obtained with a serum albumin concentration of 50-100 g/L in the solution ready for use, whereby an acceptable degree of slight oedema formation occurs in the lower end of the range. Better results are obtained with a serum albumin concentration of about 60-80 g/L in the solution ready for use, but optimal results are obtained with a concentration of 70 g/L, as stated above. If increasing to higher than 70 g/L, a higher perfusion pressure can be used without oedema formation. To achieve a perfusion flow for testing the lungs for transplantation a perfusion pressure of at most 20 mm Hg is necessary. Thus, with a view to avoiding substantial oedema formation during such a perfusion, the oncotic pressure of the solution has to be at least 5 mm Hg higher than the hydrostatic pressure.

The evaluation and preservation solution according to the present invention also comprises a scavenger and coating compound, which preferably is chosen from the group comprising dextran molecules, e.g. the commercially available Dextran 40, Dextran 60 and Dextran 70, and derivatives thereof having essentially the same structure. Dextran 40 is the most preferred scavenger and coating compound according to the present invention. Dextran molecules having other molecular weights, e.g. from as low as 1 and up to 250 kDa, more preferably from 20 and up to 150 kDa, could also be useful. However, when dextran of 1 kDa, i.e. Dextran 1, is used the concentration should be 10-140 g/L. Alternatives to Dextran 1 are lactobionate, raffinose, and mannitol, all having a molecular weight below 1 000 Da.

The scavenger and coating compound has several activities at the same time, and it acts as a coating substance for the capillary endothelium of the organ to be transplanted, as a scavenger of toxic and other undesired substances and as a detoxifying agent. For simplicity reasons, this compound is called "scavenger and coating compound" in the present application. Other compounds being scavenger and coating compounds according to the definition herein could also be present in the solution according to the present invention in combination with dextran compounds. However, pure scavenger compounds, i.e. having no or minor coating effect, also exist having a similar or better scavenging effect than the dextran compounds per se, e.g. allopurinol, vitamin C, vitamin E, didox, trimidox. Thus, such a pure scavenger or combinations thereof may be present in the solution in combination with the dextran compound, thereby obtaining an additive or synergistic effect. Further, compounds having only coating effects on the capillary endothelium, i.e. no or minor scavenging or detoxifying effect, may also be present in the solution according to the present invention in combination with the dextran compound or the pure scavenger compound, thereby obtaining an additive or synergistic effect.

Dextran compounds have turned out to be most efficient for the purpose of the present invention as they present all of the above-mentioned necessary activities. Dextran molecules are composed of glucose units in a long chain and are also provided with glucose side chains. Dextran 40 has a molecular weight (Mw) of 40,000 Da, and correspondingly the molecular weight for Dextran 60 and 70 is 60,000 and 70,000 Da, respectively. The higher the molecular weight, the longer is the dextran molecule.

The capillaries in the lungs have large pores with a diameter of about 30 nm. Gamma globulins are small enough to pass through these pores with a view to entering the capillary interstitial space to attack micro organisms and then be transported away via the lymphatic system.

The dextran molecules are not electrically charged, and they have the capability of passing through the large pores just like a worm, i.e. it is the diameter of the dextran molecule that is decisive of passage, not the length and molecular weight thereof.

When evaluating an organ which has been exposed to warm ischemia, oedema formation can be regarded as a reperfusion injury, which is substantially reduced by use of a scavenger and coating compound, preferably dextran compounds, particularly Dextran 40, in the solution due to its capability of coating the capillary membranes. As a result, it will be difficult for leucocytes to stick to the capillary endothelium and pass through the dextran molecule-coated capillaries. However, dextran molecules as such contribute partly to the oedema formation when passing through the capillary membrane pores. Thus, the dextran molecule concentration has to be optimal, i.e. the concentration should not be so high that the oedema formation is harmful, but also not so low that the overall advantageous scavenging and coating effect becomes insufficient.

Among several dextran concentrations tested for Dextran 40, a concentration in the range of 1-50 g/L in the solution ready for use has shown satisfactory results, particularly in the range of 2-20 g/L, and especially at a concentration of 5 g/L. A 3 hour evaluation test of a lung at the above-mentioned latter Dextran 40 concentration gave no weight gain of the lung, and as the evaluation and preservation solution is recirculated in the lung, it contains enough Dextran 40 to achieve effective coating of the capillary membrane. Transplanted lungs have, after evaluation and preservation with an evaluation and preservation solution according to the present invention, shown that full effect is achieved with 5 g/L Dextran 40 in the solution ready for use. In these tests a serum albumin concentration of 70 g/L was used.

As stated above, other dextran molecules are also effective, but the optimal concentration is somewhat depending on the molecular weight of a dextran molecule. However, the optimal concentration for e.g. Dextran 60 and Dextran 70 is the same or essentially the same as for Dextran 40.

Further, another compound having a function similar to those of serum albumin in this context is a particular hyaluronic acid based product, e.g. chemically modified, and variants thereof having essentially the same structure as albumin. This hyaluronic acid based product has been produced by enzymatic degradation of native hyaluronic acid, followed by controlled aggregation of the fragments and modulation to a globularily shaped product having a negative charge and a molecular weight of about 69 kDa, i.e. a product having similar size, shape and charge as serum albumin. The production of this chemically modified hyaluronic acid based product is described in e.g. EP-B-0 556 213, WO 00/46253 and WO 00/46252. This product can replace the serum albumin partially, or optionally completely, in the solution according to the present invention, still giving the effect desired. However, due to the Donnan effect discussed above the optimal concentration of the hyaluronic acid based product may vary with ±15% in relation to the dextran molecule concentration in the solutions according to the present invention. If both of these compounds are present in the solution at the same time, the sum of the concentrations thereof should not exceed 115 g/L.

The own blood from the dead human or animal from which the organ or tissue to be transplanted is donated would not be satisfactory as an evaluation and/or preservation solution. During experiments with pigs the blood of the dead pig showed shortly after death toxic products. When this blood is pumped through oxygenators and pump systems in a heart-lung machine, the complement system is activated and other toxic products are produced, whereby a lung evaluation becomes impossible.

The same activation of the complement system occurs if plasma and red blood cells, although having the correct blood grouping, from a blood bank are mixed into a solution. However, to achieve an effective evaluation red blood cells have to be added to the evaluation solution. Thus, a serum solution containing red blood cells is added as a complement to the evaluation and preservation solution according to the present invention. Preferably, washed or purified, i.e. leucocyte filtered and radiated, red blood cells from a blood bank are used. In this context, blood collected from donors is deprived of plasma and platelets. Conventionally, a CPD (citrate/phosphate/dextrose) solution is added in such a way that the erythrocyte volume fraction (EVF), also called the hematocrit value, for the red blood cells is 50%. In such a CPD solution the serum part constitutes about 78 ml and the red blood cell fraction about 222 ml. Optimal evaluation results are obtained if 300 ml of such a conventional CPD solution containing red blood cells is added per one liter of the evaluation and preservation solution according to the present invention as defined in claim 1. Thereby, due to a slight dilution effect, in such a mixed solution ready for use and to be directly added to the organ, tissue or part thereof to be evaluated, the concentration of serum albumin is 50-100 g/L, preferably 60-80 g/L, and most preferably 70 g/L. The concentration of the scavenger and coating compound in the case of dextran compounds is 1-50 g/L, preferably 2-20 g/L, and most preferably 5 g/L in the solution ready for use. For ex vivo use during the evaluation step an EVF, defining the erythrocyte volume fraction, of 15±5 vol % is attained for the mixed solution to perfuse with. The red blood cells are perfectly compatible with said solution, and their oxygen uptake and carbon dioxide emitting function is completely normal in this solution. Further, it should be noted that the conventional solution containing red blood cells should not be added to the solution according to the present invention more than about 30 minutes before the start of the perfusion due to stability problems.

Preferably, the physiologically acceptable medium comprised in the solution according to the present invention is water.

It should also be noted that the oedema formation problem described above in connection with perfusion during lung evaluation is particularly pronounced for lungs. The same problem arises correspondingly for other organs and tissues to be transplanted, but to a smaller extent.

In transplantation surgery of a non-heart-beating donor patient, e.g. a person who has died in an acute heart arrest, the organ or tissue to be transplanted, e.g. a lung, has to be cooled when still present in the dead body within two hours, preferably one hour, from the death. The lungs of the donor body can be cooled at a temperature of 8-12° C. without risk of injury the next 24 hours. To obtain this cooling of lungs, the pleura is initially perfused with a conventional solution for this purpose, e.g. Perfadex solution.

Thereafter, the lung is harvested from the donor body and is placed in a heart-lung machine comprising a pump, an oxygen supply, an oxygenator, and a respirator. The lung is then filled with the mixed solution of the evaluation and preservation solution according to the present invention and the serum solution containing red blood cells, having an EVF of 15±5 vol %. Then the lung is evaluated with a view to deciding whether it is acceptable for transplantation, i.e. the blood gases, the vascular resistance, the endothelial function, the lung compliance, any ventilation/perfusion disorders, the gas output, and the surfactant function is evaluated. If acceptable, the lung is transplanted into the receiver body and has all of its important physiological functions and activities kept intact. This kind of lung, evaluation and transplantation has never been done until now, i.e. a successful transplantation of a lung from a non-heart-beating donor and evaluation in the way described above.

The evaluation and preservation solution according to the present invention also works for the evaluation of all organs and tissues of the human and animal body, in extreme also for the whole human or animal body as such and also for all organs and tissues from traditional brain-dead but heart-beating donors of both human and animal origin, and gives also better results than all other corresponding solutions known so far. It is useful for all organs in the preservation aspect except, the heart. If used to preserve the heart for cold ischemic storage, the potassium concentration has to be raised to 16-30 mmol/l, preferably 20-26 mmol/l, and most preferably 23 mmol/l. This general application for all organs and tissues can be explained by the fact that as the solution according the present invention is highly efficient for the evaluation of lungs, which are known to be most sensitive of all organs due to the large capillary membrane pores, then it has to be effective on all other organs due to their smaller pores.

For heart evaluation, the potassium concentration in the solution according to the present invention has to be increased from the normal level of about 4.5 up to about 23, thereby achieving cardioplegia.

Non-exhaustive examples of organs and tissues of most interest to be transplanted and therefore first evaluated are lung(s), hearts, livers, kidneys, pancreas, small bowel, body extremities, etc.

The mixed solution ready for use according to the present invention should be run through a pump giving physiological perfusion pressure in the organ to be transplanted. Further, the solution should pass through an oxygenator to supply the red blood cells with oxygen and take up the $CO_2$. If plasma with red blood cells from a blood bank is used in a closed circle with oxygenators and plastic tubes, the activation of the complement system, substances and other toxic systems precludes stable perfusion.

The solutions according to the present invention lacks toxic properties when used in a closed evaluation system including oxygenators and pumps. In such way the organ to be transplanted can be perfused for 24 hours or more, during which time no ischemia occurs. During tests hearts have been preserved with the mixed solution ready for use according to the present invention (with a potassium concentration of 23 mmol/l), which has been oxygenated by an oxygenator and pumped through the heart for 24 hours, followed by transplantation of the heart, which showed perfect function from the very beginning. If the preservation and evaluation solution according to the present invention is mixed with red blood cells to an EVF of 15±5 vol %, lungs from non-heart-beating donors can be evaluated and after the evaluation the lungs can be preserved for at least 36 hours before transplantation by cold ischemic storage at 4° C.

Examples of two preferred evaluation and preservation solutions according to the present invention are the following:

One preferred embodiment of the evaluation and preservation solution according to the present invention consists of the following components in the concentrations shown.

| Component | Concentration |
| --- | --- |
| Dextran 40 | 5 g/L |
| Sodium chloride | 98 mmol/L |
| Potassium chloride | 0.49 mmol/L |
| Calcium chloride | 1.4 mmol/L |
| Magnesium sulphate | 1.2 mmol/L |
| Potassium dihydrogen phosphate | 0.042 mmol/L |
| Dipotassium hydrogen phosphate anhydrate | 0.84 mmol/L |
| Disodium hydrogen phosphate dihydrate | 0.029 mmol/L |
| Sodium bicarbonate | 14 mmol/L |
| Potassium acetate | 2.9 mmol/L |
| Glucose monohydrate | 10 mmol/L |
| Albumin Centeon (200 mg/ml) | 64 g/L |
| Sodium hydroxide (1M) | |
| Sterile water | |

The components are dissolved in sterile water and pH is adjusted to 7.4 with sodium hydroxide.

Another preferred embodiment of the evaluation and preservation solution according to the present invention consists of the following components in the concentrations shown.

| Component | Concentration |
| --- | --- |
| Dextran 40 | 5 g/L |
| Sodium chloride | 86 mmol/L |
| Potassium chloride | 4.6 mmol/L |
| Calcium chloride dihydrate | 1.5 mmol/L |
| Sodium dihydrogen phosphate dihydrate | 1.2 mmol/L |
| Sodium bicarbonate | 15 mmol/L |
| Magnesium dichloride hexahydrate | 1.2 mmol/L |
| D(+)-glucose monohydrate | 11 mmol/L |
| Human serum albumin (200 g/l) | 70 g/L |
| Sodium hydroxide (1M) | |
| Sterile water | |

The components are dissolved in sterile water and pH is adjusted to 7.4 with sodium hydroxide. The mixed solution ready for use according to the present invention is obtained by mixing each of the both preferred embodiment solutions (1 000 ml) with 300 ml of the above described CPD solution.

The most preferred evaluation and preservation solution according to the present invention for a heart is similar to that for lungs, but has a higher potassium concentration, as defined above.

Experiments

A weight gain of the lung during the evaluation step before transplantation, is significant for undesired oedema formation, which occur when a test solution not containing the correct concentrations of serum albumin is used.

Different experiments have been performed for evaluation solutions containing different components during the evaluation of a lung. The weight gain (expressed in kg) was measured against time during a constant perfusion flow rate.

A solution ready for use containing neither serum albumin, nor scavenger and coating compound gave a significant weight gain, showing the shortages of such a solution, as shown in FIG. 1.

A solution ready for use containing Dextran 40, but no human serum albumin, gave an even more substantial weight gain by time, as shown in FIG. 2.

A solution ready for use containing 70 g/L human serum albumin, but no Dextran 40, gave an unsatisfactory weight gain by time, as shown in FIG. 3.

A solution ready for use containing 35 g/L of serum albumin and 25 g/L of Dextran 40 gave an unsatisfactory weight gain by time. This weight gain depends on the too high concentration of Dextran D 40, i.e. 25 g/L and the too low concentration of albumin, i.e. 35 g/L.

A solution ready for use containing 70 g/L of serum albumin and 5 g/L of Dextran 40 gave no weight gain by time. This solution represents a mixed solution ready for use according to the present invention, i.e. both the serum albumin and the Dextran 40 in correct concentrations.

The present invention also refers to a method for evaluating an organ or a tissue to be transplanted, wherein said organ or tissue is perfused with the evaluation and preservation solution according to the present invention mixed with the serum solution containing red blood cells, followed by evaluation of the organ or tissue, and optional preservation in the same solution until transplantation. For lungs the perfusion flow rate during the evaluation is about 4 liters/min, the temperature is about 37° C. and the maximum perfusion pressure is about 20 mm Hg. The perfusion flow rate is lower when perfusing other organs. For the evaluation of a kidney, the perfusion pressure must be as high as about 90 mm Hg.

The present invention also refers to a method of transplantation of an organ, tissue or a part thereof from a non-heart-beating human or animal donor, in which the organ, tissue or part thereof is harvested from the donor body, is perfused with the evaluation and preservation solution according to the present invention mixed with the serum solution containing red blood cells, the organ or tissue or part thereof is evaluated, and, if the organ, tissue or part thereof is acceptable for transplantation, it is preserved in said solution until transplantation. Preferably, said organ is a lung.

It should also be noted that the evaluation and preservation solution according to the present invention is applicable to all kinds of transplantation, e.g. auto-, allo- and xenotransplantation.

The invention claimed is:

1. A method of perfusing an organ, tissue, or part thereof, of an animal or human, the method comprising:
   (1) evaluating the organ, tissue, or part thereof; and
   (2) perfusing the organ, tissue, or part thereof at normothermia by recirculation with a solution; wherein the solution comprises:
      (a) a colloidosmotically active substance that is too large to pass out through semipermeable capillary walls of the animal or human and that is present at a concentration that provides the oncotic pressure of serum albumin at a concentration of 55-105 g/L;
      (b) a scavenger and coating compound, which coats the capillary endothelium of the organ, tissue, or parts thereof, at a concentration of 1-55 g/L;
      (c) a physiological serum concentration of a salt; and
      (d) a nutrient for the organ, tissue, or part thereof,
   in a physiologically acceptable medium; and
   further wherein the evaluating comprises measuring evaluation parameters of the organ, tissue, or part thereof for transplantation thereof;
   the solution provides an oncotic pressure higher than an applied hydrostatic pressure in the organ, tissue, or part thereof, and prevents oedema formation; and
   the organ, tissue, or part thereof is connected to a heart-lung machine during the perfusion.

2. The method of claim 1, wherein the organ is a lung, a heart, a kidney, a liver, a pancreas, or small bowels.

3. The method of claim 1, further comprising preserving the organ, tissue or part thereof in said solution until the transplantation.

4. The method of claim 1, wherein the organ is a lung.

5. The method of claim 1, wherein the organ, tissue, or part thereof is harvested from a non-heart-beating animal or human donor, and the evaluating further comprises evaluating if the organ, tissue, or part thereof is acceptable for transplantation; and further comprising transplanting the organ, tissue, or part thereof into a receiver body.

6. The method of claim 5, further comprising preserving the organ, tissue, or part thereof in the solution until the transplantation.

7. The method of claim 5, wherein the organ, tissue, or part thereof is auto-, allo- or xenotransplanted.

8. The method of claim 1, wherein the colloidosmotically active substance has a negative charge and a molecular weight of about 69 kDa.

9. The method of claim 1, wherein the colloidosmotically active substance is a hyaluronic acid-based compound having a molecular weight of about 69 kDa.

10. The method of claim 1, wherein the colloidosmotically active substance is present in the solution at a concentration that provides the oncotic pressure of serum albumin at a concentration of 65-85 g/L.

11. The method of claim 1, wherein the colloidosmotically active substance is present in the solution at a concentration that provides the oncotic pressure of serum albumin at a concentration of 70 g/L.

12. The method of claim 1, wherein the scavenger and coating compound has a molecular weight ranging from 1 to 250 kDa.

13. The method of claim 1, wherein the scavenger and coating compound has a molecular weight ranging from 15 to 115 kDa.

14. The method of claim 1, wherein the scavenger and coating compound has a molecular weight ranging from 20 to 150 kDa.

15. The method of claim 1, wherein the concentration of the scavenger and coating compound in the solution is 2-20 g/L.

16. The method of claim 1, wherein the concentration of the scavenger and coating compound in the solution is 5 g/L.

17. The method of claim 1, wherein the salt comprises one or more of sodium, potassium, calcium, magnesium, phosphate, hydrogen carbonate, and chloride ions; and the nutrient comprises one or more of a physiologically acceptable carbohydrate, fatty acid, and amino acid.

18. The method of claim 17, wherein the physiologically acceptable carbohydrate is glucose.

19. The method of claim 1, wherein the solution further comprises at least one of the following: a vasodilator; an antibiotic; a fibrinolytic component; a thrombocyte receptor blocker; a hormone; an insulin; a cortisol; a growth hormone; and an anabolic steroid.

20. The method of claim 1, wherein the solution further comprises a pure scavenger compound.

21. The method of claim 1, wherein the solution further comprises papaverine, alteplase, abciximab, tyroxin/triiodotyronin, or a combination thereof.

22. The method of claim 12, wherein the scavenger and coating compound is a dextran compound.

23. The method of claim 13, wherein the scavenger and coating compound is a dextran compound.

24. The method of claim 14, wherein the scavenger and coating compound is a dextran compound.

* * * * *

UNITED STATES PATENT AND TRADEMARK OFFICE
CERTIFICATE OF CORRECTION

PATENT NO. : 8,980,541 B2  
APPLICATION NO. : 13/178655  
DATED : March 17, 2015  
INVENTOR(S) : Steen Page 1 of 1

It is certified that error appears in the above-identified patent and that said Letters Patent is hereby corrected as shown below:

In the specification:

Column 4, line 14, the text "1.0" should read --10--.

Signed and Sealed this  
Twenty-ninth Day of September, 2015

Michelle K. Lee  
*Director of the United States Patent and Trademark Office*